US005889148A

United States Patent [19]
Lee et al.

[11] Patent Number: 5,889,148
[45] Date of Patent: Mar. 30, 1999

[54] ANTIBIOTIC PEPTIDES

[75] Inventors: Keun-Hyeung Lee, Seoul; Sung-Yu Hong; Hyun-Sook Cho, both of Kyonggi-Do; Bok-Leul Lee, Pusan; Kwang-Hoe Chung; Jeong-Hyeok Yoon, both of Kyonggi-Do; Jong-Eun Oh, Seoul; Hong-Mo Moon, Kyonggi-Do, all of Rep. of Korea

[73] Assignee: Mogam Biotechnology Research Institute, Kyonggi-Do, Rep. of Korea

[21] Appl. No.: 700,449

[22] PCT Filed: Mar. 11, 1996

[86] PCT No.: PCT/KR96/00034

§ 371 Date: Aug. 27, 1996

§ 102(e) Date: Aug. 27, 1996

[87] PCT Pub. No.: WO97/02286

PCT Pub. Date: Jan. 23, 1997

[30] Foreign Application Priority Data

Jul. 6, 1995 [KR] Rep. of Korea ............... 95-19694
Jan. 29, 1996 [KR] Rep. of Korea ............... 96-1909
Jan. 29, 1996 [KR] Rep. of Korea ............... 96-1910
Jan. 29, 1996 [KR] Rep. of Korea ............... 96-1911

[51] Int. Cl.$^6$ .................... A61K 38/00; C07K 5/00; C07K 7/00; C07K 15/00
[52] U.S. Cl. .................... 530/326; 530/327; 530/328; 514/13; 514/14; 514/15; 514/16
[58] Field of Search .................... 514/13, 14, 15, 514/16; 530/326, 327, 328

[56] References Cited

FOREIGN PATENT DOCUMENTS

| 0349451 | 1/1990 | European Pat. Off. .......... C07K 7/10 |
| 0 665 239 A1 | 8/1995 | European Pat. Off. . |
| 9702286 | 1/1997 | WIPO ............... C07K 7/04 |

OTHER PUBLICATIONS

Gibson, B.W. et al., Novel Peptide Fragments Originating from PGL and the Caerulein and Xenopsin Precursors from *Xenopus laevis*, *J. Biol. Chem.*, 261(12):5341–5349 (1986).
Lee, J.-Y. et al., Antibacterial Peptides from Pig Intestine: Isolation of a Mammalian Cecropin, *Proc. Natl. Acad. Sci., USA* 86:9159–5162 (1989).

Zasloff, M. et al., Antimicrobial Activity of Synthetic Magainin Peptides and Several Analogues, *Proc. Natl. Acad. Sci., USA*, 95:910–913 (1988).
Simmaco, M. et al., Antimicrobial Peptides from Skin Secretions of *Rana escultenta*, *J. Biol. Chem.*, 269(16):11956–11961 (1994).
Zasloff, M. Magainins, a Class of Antimicrobial Peptides from Xenopus Skin: Isolation, Characterization of Two Active Forms, and Partial cDNA Sequence of a Precursor, *Proc. Natl. Acad. Sci., USA*, 84:5449–5453 (1987).
Dimarcq, J.L. et al., Insect Immunity: Expression of the Two major Inducible Antibacterial Peptides, Defensin and Diptericin, in *Phormia terranovae*, *EMBO J.*, 9(8):2507–2515 (1990).
Romeo, D. et al., Structure and Bactericidal Activity of an Antibiotic Dodecapeptide Purified from Bovine Neutrophils, *J. Biol. Chem.*, 263(2):9573–9575 (1988).
Steiner, H. et al., Sequence and Specificity of Two Antibacterial Proteins Involved in Insect Immunity, *Nature*, 292:246–248 (1981).
Matsuyama, K. and Natori, S., Purification of Three Antibacterial Proteins from the Culture Medium of NIH–Sape–4, an Embryonic Cell Line of *Sarcophaga peregrina*, *J. Biol. Chem.*, 263(32):17112–17116 (1988).
Chopra, I., The Magainins: Antimicrobial Peptides with Potential for topical Application, *Journal of Antimicrobial Chemotherapy*, 32:351–353 (1993).
Moon, H.J. et al., Purification and Molecular Cloning of cDNA for an Inducible Antibacterial Protein from Larvae of the Coleopteran, *Tenebrio molitor*, *The Journal of Biochemistry*, 16(1):53–58 (1994).
Jung, Y.H. et al., Biochemical and Molecular Characterization of an Antifungal Protein from Tenebrio Molitor Larvae, *Chemical Abstracts*, vol 123, No. (1995).

Primary Examiner—Avis M. Davenport
Attorney, Agent, or Firm—Darby & Darby

[57] ABSTRACT

The present invention relates to novel antibiotic peptides which possess antibacterial and/or antifungal activities causing no cytotoxicity, and to antibacterial and/or antifungal agents containing said peptides as active ingredients. In accordance with the present invention, it has been discovered that a number of chemically-synthesized peptides which are derived from Tenecin, show superior antibacterial and/or antifungal activities, while causing no untoward effects, and they can be applied for the development of antibacterial and/or antifungal agents.

2 Claims, No Drawings

ANTIBIOTIC PEPTIDES

This application is a '371 of PCT/KR96/00034 filed Nov. 3,1996.

FIELD OF THE INVENTION

The present invention relates to novel antibiotic peptides which possess superior antibacterial and/or antifungal activities while causing no cytotoxicity, and to antibacterial and/or antifungal agents containing said peptides as active ingredients.

DESCRIPTION OF THE PRIOR ART

More than 100 years have elapsed since the first scientific demonstration of microbial antagonism and five decades since the first clinical use of penicillin. At present, several thousand antibiotics are known and many of them are in practical use. However, studies on the antibiotics have been continuously needed due to the appearance of mutant microorganisms acquired resistance to the antibiotics and the serious side-effects of the commercially available antibiotics. In this regard, attempts to develop novel antibiotics to solve said problems have been carried out by screening secondary metabolites of microorganisms, by synthesizing analogues of known antibiotics such as quinolones or by isolating antibiotics such as proteins or peptides induced by an intracelluar defense mechanism (see Natori S., J. Insect Physiol., 23:1169–1173(1977); Okada M. & Natori S., Biochem. J., 211:727–734(1983); Ando K. et al., Biochemistry, 260:7174–7177(1987); Steiner H. et al., Nature, 292:246–248(1981); Casteels, P. et al., Eur. J. Biochem., 187:381–386(1990)).

On the other hand, it has been known that insects protect themselves from pathogenic bacteria or parasites by their own cellular and humoral immune systems, and they frequently respond to the attack of pathogens by producing antibiotics, e.g., antibacterial proteins or peptides. Until now, about 50 antibacterial proteins or peptides have been isolated from the insects and their structures have been also elucidated. Some of the self-protective proteins or peptides such as Cecropin, have been intensively studied, which provides basic ideas for the development of antibacterial substances whose modes of action are novel.

It has been also reported that most of antibacterial proteins or peptides may target lipid membrane, even though biological activities of all the antibacterial substances are not clearly understood. For example, Cecropin, which is appeared in the hemolymph of certain insects, shows its activity on Gram positive and negative bacteria, by the amphiphilic binding with lipid membrane of bacteria, to form ion channels diverse in size and to allow a rupture of cell membrane(see: Christensen, B. et al., Proc. Natl. Acad. Sci., USA, 85:5072–5076(1988)).

In addition to Cecropin, cysteine-containing Defensin and Sapecin, which are isolated from insects, are fallen within the antibacterial peptides whose target site are lipid membrane of Gram positive bacteria(see: Kuzuhara, T. et al., J. Biochem., 107:514–518(1990)). Their modes of action have been anticipated to be different from Cecropin, in light of the previous finding that insect Defensin leads to bacterial cell lysis in a relatively slower manner than Cecropin which requires only 1 min to reach cell rupture.

Another antibacterial peptides whose target site are lipid membrane, includes Attacin, Sarcotoxin, Deftericin, Coleoptericin, Apidaecin and Abaecin. The peptides conserve G and P domains, and have an influence on the cell differentiation of Gram negative bacteria and, in turn, lead to chain-shaped cell growth. In particular, Attacin has been also reported to break down outer membrane of the targeted bacteria by inhibiting the synthesis of outer membrane proteins.

Besides the antibacterial peptides of insects illustrated as above, several antibiotic peptides have been also isolated from amphibia, e.g., Magainin (see: Zasloff, M., Proc. Natl. Acad. Sci., USA, 84:5449–5453(1987), Ranalexin (see: Clark., D. P. et al., J. Biol. Chem., 269:10849–10855 (1994)), Brevinins (see: Morikawa, N. et al., Biochem. Biophys. Res. Commun., 189:184–190(1992)) and Esculantins (see: Simmaco, M. et al., FEBS Lett., 324:159–161 (1993)). The peptides have been known to show their antibacterial activities in a similar mechanism to Cecropin, i.e., forming ion channels in lipid membrane of bacteria to rupture the cell.

On the other hand, the present inventors have previously reported the isolation of a protein which shows antibacterial activity(hereinafter referred to as "Tenecin") from a larva of *Tenebrio molitor* on which *E. coli* is infected(see: Lee, B. L. et al., J. Biochem., 116:53–58(1994)) whose amino acid sequences are:

V T C D I L S V E A K G V K L N D A A C A A H C-LFRGRSGGYCNGKRVCVCR—$CO_2H$

However, the practical use of Tenecin have encountered several serious problems as followings: Tenecin should be isolated from the larva of *Tenebrio molitor*, which makes its isolation and mass production difficult; a large molecular size of Tenecin may provoke antigen-antibody reaction in vivo; Tenecin have narrow spectrum of target cell, i.e., on Gram positive bacteria only; and, Tenecin is unstable since its chemical nature is protein.

Under the circumstances, in order to provide novel antibacterial substances to overcome the problems of Tenecin discussed above, the present inventors have synthesized peptide fragments of Tenecin and their chemical analogues by the addition, deletion or substitution of amino acids, based on a finding that active site of Tenecin is conserved on a specific region, and finally discovered that the peptides possess superior antibacterial and antifungal activities while causing no untoward effects such as cell lysis.

SUMMARY OF THE INVENTION

In accordance with the present invention, the inventors discovered that: a number of chemically-synthesized peptides which are derived from Tenecin, show superior antibacterial and/or antifungal activities, while causing no untoward effects, and they can be applied for the development of antibacterial and/or antifungal agents.

A primary object of the present invention is, therefore, to provide novel antibiotic peptides which possess superior antibacterial and/or antifungal activities while causing no cytotoxicity.

The other object of the invention is to provide antibacterial and/or antifungal agents containing said peptides as active ingredients.

DETAILED DESCRIPTION OF THE INVENTION

The present invention provides acid- or amide-form peptides which possess both antibacterial and antifungal activities, which are represented by the general formula(I), formula(II) and formula(III) as below, and analogues thereofs including enantiomers, retro-inversoes and derivatives where at most 3 neighboring amino acids located in each of N- and/or C-terminals, or at most 2 neighboring amino acids in the mid-part of the peptides, are substituted with D-form amino acids, respectively:

$$\alpha^1 \alpha^2 \alpha^3 \alpha^4 \alpha^5 \text{ V C V C } \alpha^6 \qquad (I)$$

wherein,
- $\alpha^1$ is 2 to 4 residues of amino acid, which are preferably selected from the group consisting of YC, FC, WS, FYC, KYC, PYC, KFYC and FFYC;
- $\alpha^2$ is N, K or V;
- $\alpha^3$ is vacant, or G, P, L or K;
- $\alpha^4$ is vacant or K;
- $\alpha^5$ is vacant or R;
- $\alpha^6$ is R, L or D; and,
- C may be replaced with aminoisobutyric acid.

$$\beta^1 \beta^2 \beta^3 \beta^4 \beta^5 \beta^6 \beta^7 \beta^8 \beta^9 \beta^{10} \qquad (II)$$

wherein,
- $\beta^1$ is vacant, or 1 or 2 basic amino acids;
- $\beta^2$ is vacant, or 1 or 2 hydrophobic or basic amino acids (provided that $\beta^1$ is vacant and $\beta^2$ is 1 residue of amino acid, Pro and Tyr are excluded);
- $\beta^3$ is 2 amino acids selected from the group consisting of hydrophobic amino acids and Cys;
- $\beta^4$ is 1 or 2 amino acids (provided that $\beta^4$ is 1 residue of amino acid, Pro and acidic amino acids are excluded; and, provided that $\beta^4$ is 2 amino acids, both of which should not be acidic amino acids);
- $\beta^5$ is 1 or 2 basic amino acids;
- $\beta^6$ is vacant, or a hydrophobic amino acid;
- $\beta^7$ is an amino acid selected from the group consisting of hydrophobic aromatic and aliphatic amino acids, Cys and Ser;
- $\beta^8$ is a hydrophobic amino acid;
- $\beta^9$ is an amino acid selected from the group consisting of hydrophobic aromatic and aliphatic amino acids, Cys and Ser (provided that $\beta^7$ is a hydrophobic aliphatic amino acid or Ser, $\beta^9$ should be a hydrophobic aromatic amino acid or Cys); and,
- $\beta^{10}$ is 1 or 2 basic amino acids.

$$\gamma^1 \gamma^2 \gamma^3 \gamma^4 \gamma^5 \qquad (III)$$

wherein,
- $\gamma^1$ is 1 to 4 residues of amino acid;
- $\gamma^2$ is 2 to 4 hydrophobic amino acids;
- $\gamma^3$ is 1 or 2 basic amino acids;
- $\gamma^4$ is 2 to 4 hydrophobic amino acids; and,
- $\gamma^5$ is 1 to 3 amino acids containing at least one of basic amino acids (provided that $\gamma^5$ is more than 2 amino acids, basic amino acids are directed to N-terminal).

The present invention also provides acid- or amide-form peptides which possess antifungal activity, which are represented by the general formula(IV) as below, and analogues thereofs including enantiomers, retro-inversoes and derivatives where at most 3 neighboring amino acids located in each of N- and/or C-terminals, or at most 2 neighboring amino acids in the mid-part of the peptides, are substituted with D-form amino acids, respectively:

$$\delta^1(ab)_{n1}(ba)c\delta^2 \qquad (IV)$$

wherein,
- $\delta^1$ is 1 to 4 residues of amino acid;
- a is a hydrophobic aromatic amino acid;
- b is a hydrophobic aliphatic amino acid;
- n1 is an integer of 1 or 2;
- n2 is an integer of 1, 2 or 3 (provided that n1 is 1, n2 is 2 or 3; and, provided that n1 is 2, n2 is 1 or 2);
- c is vacant, or a hydrophobic amino acid; and,
- $\delta^2$ is 1 or 2 basic amino acids.

In describing the antibiotic peptides of the present invention, one-letter abbreviation of amino acids is employed, in accordance with the nomenclature system of the IUPAC-IUB.

Further, the term basic amino acids are employed to mean usual or unusual amino acids with a basic side chain, e.g., His, Lys & Arg as an usual and 2-methyl-L-arginine, ornithine, 2,3-diaminopropionic acid and 2,4-diaminobutyric acid as an unusal.

Hydrophobic amino acids are employed to mean both aromatic and aliphatic amino acids, where the hydrophobic aromatic amino acids contain usual or unusual amino acids with an aromatic functional group, e.g., Phe, Tyr, Trp & Pro as an usual and L-3-(2,5-dihydrophenyl)-alanine, L-β-(5-hydroxy-2-pyridyl)-alanine and β-isotyrosine as an unusual; and, the hydrophobic aliphatic amino acids contain usual or unusual amino acids with an aliphatic functional group, e.g., Gly, Ala, Val, Leu & Ile as an usual and aminoisobutyric acid, isovaline, norleucine, norvaline, 2-amino-5-methylhexanoic acid, 2-amino-6-methylheptanoic acid, 2-amino-7-methyloctanoic acid as an unusual.

Acidic amino acids are employed to mean usual or unusual amino acids with an acidic functional group, e.g., Asp & Glu as an usual.

Usual amino acids are employed to mean naturally occurring 20 amino acids named in conformity with the IUPAC-IUB nomenclature system, and unusual amino acids are all the amino acids except for said naturally occurring 20 usual amino acids.

Though peptides are synthesized chemically in the present invention, they can also be prepared from the host cells transformed with proper recombinant plasmids containing the nucleotide sequences which are reversely deduced from the amino acid sequences of peptides of interest.

Based on the determination of minimal inhibition concentrations (MICs) against test organisms, i.e., bacteria and fungi, it has been found that peptides of the invention possess excellent antibacterial and/or antifungal activities. Further, from the absorbance measurement after coincubation of red blood cells and the peptides, it has been also found that the peptides do not give rise to lyse the red blood cells.

From the above results, it has been concluded that: the antibiotic peptides of the invention can be applied for the development of antibacterial and antifungal agents for the chemotherapy of local and systemic infections caused by pathogenic bacteria and/or fungi; and, they can be formulated into potent antibacterial and/or antifungal agents with pharmaceutically acceptable carriers.

For oral administration, the peptides can be formulated into a solid preparation such as tablets, pills, granules, powder, capsules and the like, or a liquid preparation such as solutions, suspensions, emulsions and the like. The pharmaceutical preparations for oral administration can contain active peptide or peptides alongside the customary excipients such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerine, (d) disintegrating agents, for example agar- agar, calcium carbonate and sodium carbonate, (e) solution retarders, for example paraffin, (f) absorption accelerators, for example quaternary ammonium compound, (g) wetting agents, for example cetyl alcohol or glycerine monostearate, (h) adsorbents, for example kaolin and bentonite, (i) lubricants, for example talc, calcium stearate and magnesium stearate and solid polyethylene glycols, (j) colorants, (k) flavourings, (l) sweeteners, or mixtures of the substances listed under (a) to (l).

When the preparation is used for parental administration, the preparation is made in an injection formula, an intravenous drip infusion and the like. For the preparation of an injection formula, the solutions and emulsions can be in a sterile form which is isotonic with blood. The suspensions can contain in addition to the active peptide or peptides, preservatives, stabilizers, solubilisers, wetting agents, salts for changing the osmotic pressure or buffers.

The present invention is further illustrated in the following examples, which should not be taken to limit the scope of the invention.

EXAMPLE 1

Chemical Synthesis of Peptide Fragments of Tenecin and Determination of Active Site In order to determine the locus of active site, a number of peptide fragments of Tenecin were chemically synthesized from N-terminal to C-terminal, in accordance with the solid phase synthesis method:

The peptides were synthesized by employing a peptide synthesizer(Applied Biosystem Instrument, Model 431A, USA). For the chemical synthesis, free amino acids were coupled to Fmoc(9-fluorenylmethoxycarbonyl) group for N-terminal protection, and Trt(trityl), Boc (butyloxycarbonyl), tBu(t-butylester) or Pmc (pentamethylchroloman) group for protection of reactive side chains. Amino acids thus protected includes: Fmoc-L-Ala, Fmoc-L-Arg(Pcm), Fmoc-L-Asn(Trt), Fmoc-L-Asp (tBu), Fmoc-L-Cys(Trt), Fmoc-L-Gly, Fmoc-L-Glu(tBu), Fmoc-L-Gln(Trt), Fmoc-L-His(Trt), Fmoc-L-Ile, Fmoc-L-Leu, Fmoc-L-Lys(Boc), Fmoc-L-Phe, Fmoc-L-Ser, Fmoc-L-Thr(tBu) and Fmoc-L-Val.

In order to increase the stability of synthesized peptides, PAL(5-(4-amino)methyl-3,5-dimethoxyphenoxyvaleric acid) and WANG(4-alkoxybenzyl alcohol) resins were employed, to give peptides having amide- and acid-forms of C-terminal upon cleavage from the resins, respectively, where 0.1 mmole of the resin and 0.5 mmole of amino acids were preferably added.

HOBt(N-hydroxybenzotriazole) and DCC (N,N'-dicyclohexyl carbodiimide) were employed as a carboxyl group activator in coupling of amino acids. After the completion of coupling for about 35 min, Fmoc N-terminal protecting group was removed by the treatment of piperidine. On the other hand, the side chain protected peptide on the solid support resin, was reacted with a cleavage solution (containing 80% TFA(trifluoroacetic acid), 2.5% ethanedithiol, 5% thioanizole, 7.5% phenol and 5% $H_2O$) for 8hrs at room temperature, and then, the peptide from which side chain protecting group was removed, was isolated from the resin. A solution containing the synthesized peptide was obtained by filtration and TFA was removed by purging nitrogen gas. To the resultant, diethylether chilled at −20° C. was added and then centrifuged at 3,000 rpm for 20 min to precipitate the peptide.

Peptides thus prepared were purified with the aid of preparative HPLC equipped with reverse phase $C_{18}$ column (Delta Pak C18-300A,, 1.9×30 cm, Waters, USA) by eluting with a linear gradient of acetonitrile in 0.1% TFA at a flow rate of 20 mL/min, and their molecular weights were determined by mass spectroscopy.

Antibacterial and antifungal activities of the peptide fragments of Tenecin thus synthesized, were determined by MIC tests employing test organisms, i.e., *Staphylococcus aureus* and *Candida albicans*, as fully described in Example 2 below. Amino acid sequences of the peptides and their antibacterial and antifungal activities were disclosed in

TABLE 1

Peptide fragments of Tenecin and antibiotic activity thereofs

| | | | MIC($\mu$g/ml) | |
| --- | --- | --- | --- | --- |
| Name | Amino acid sequence | Location in Tenecin | *S. aureus* | *C. albicans* |
| TEA | DAACAAHHCLFR—$NH_2$ (SEQ ID NO:2) | middle | >500 | >100 |
| TEB | NDAACAAHCLFRGRSGG—$NH_2$ (SEQ ID NO:3) | middle | >500 | >100 |

TABLE 1-continued

Peptide fragments of Tenecin and antibiotic activity thereofs

| | | | MIC($\mu$g/ml) | |
|---|---|---|---|---|
| Name | Amino acid sequence | Location in Tenecin | S. aureus | C. albicans |
| TEC | VTCDILSSVEAKGVKL—NH$_2$ (SEQ ID NO:4) | N-terminal | >500 | >100 |
| TED | YCNGKRVCVCR—NH$_2$ (SEQ ID NO:5) | C-terminal | 10 | 10 |
| TEO | LSVEAKGVKLNDAACAAHCL–NH$_2$ (SEQ ID NO:6) | middle | >500 | >100 |
| TEQ | LSVEAKGVKLGGGYCNGKRVCVCR—NH$_2$ (SEQ ID NO:7) | middle and C-terminal | >500 | >100 |
| Tenecin | VTCDILSVEAKGVKLNDAACAAHCLFRGR-SGGYCNGKRVCVCR—CO$_2$H (SEQ ID NO:1) | | 3 | >500 |

As can be seen in Table 1, it was surprisingly determined that TED possesses an excellent antifungal activity which is not appeared in Tenecin, though all of the peptide fragments showed lower antibacterial activity than that of intact Tenecin.

To improve antibacterial and antifungal activities of the peptides, based on the results above, amino acids were added to N-terminal of the TED peptide: for example, TEDF was prepared by adding Phe to N-terminal of the TED peptide, and TEDFK was prepared by adding Phe and Lys to N-terminal. TED, TEDF and TEDFK thus prepared further underwent a multiplicity of addition, deletion and replacement of amino acids in the following examples.

EXAMPLE 2

Determination of Antibacterial and Antifungal Activities

Antibacterial and antifungal activities of the peptides were determined by employing MIC test as follows:

To determine antifungal activity, a test organism *Candida albicans* (ATCC 36232) was cultured on Sabouraud dextrose agar plate for 24 to 48 hrs, and colonies thus grown were suspended on Sabouraud dextrose medium(Gibco, USA) to have O.D.$_{530}$=0.5(3×10$^6$ cells) and further diluted with 100-fold to have O.D.$_{530}$=0.005(3×10$^4$ cells). 100 $\mu$l of *Candida albicans* culture thus prepared was pipetted on 96-well microplates which had already contained 100 $\mu$l of a serially diluted peptide solution. After incubation at 30° C. for 24 hrs, absorbance at 530 nm was observed to determine the MIC of peptide against *Candida albicans*.

Antibacterial activity of peptide was determined analogously as above, with an exception that *Staphylococcus aureus* (ATCC 6538) selected as a test organism was cultured on M-3 medium(Gibco, USA) at 37° C. and cell number was adjusted to 2×10$^8$ cells before 100-fold dilution.

A number of peptides whose antibacterial and antifungal activities were determined as aboves, were shown in Tables 2, 3, 4, 5 and 6.

TABLE 2

Modification of N-terminal amino acid residues of the TED peptide

| Name | Amino acid sequence | MIC($\mu$g/ml) against C. albicans |
|---|---|---|
| TED | YCNGKRVCVCR—NH$_2$ (SEQ ID NO:5) | 10 |
| TED11 | GKRVCVCR—NH$_2$ (SEQ ID NO:8) | >500 |
| TED12 | KGKRVCVCR—NH$_2$ (SEQ ID NO:9) | >500 |
| TED13 | HGKRVCVCR—NH$_2$ (SEQ ID NO:10) | >500 |
| TED14 | SNGKRVCVCR—NH$_2$ (SEQ ID NO:11) | 30 to 50 |
| TED15 | CNGKRVCVCR—NH$_2$ (SEQ ID NO:12) | >500 |
| TED16 | FCNGKRVCVCR—NH$_2$ (SEQ ID NO:13) | 10 to 20 |
| TED17 | LCNGKRVCVCR—NH$_2$ (SEQ ID NO:14) | 100 |
| TED18 | KCNGKRVCVCR—NH$_2$ (SEQ ID NO:15) | >500 |
| TED19 | WSNGKRVCVCR—NH$_2$ (SEQ ID NO:16) | 10 to 20 |

TABLE 3

Addition of an amino acid to N-terminal of the TED peptide

| | | MIC($\mu$g/ml) | |
|---|---|---|---|
| Name | Amino acid sequence | S. aureus | C. albicans |
| TED | YCNGKRVCVCR—NH$_2$ (SEQ ID NO:5) | 10 | 10 |
| TEDF | FYCNGKRVCVCR—NH$_2$ (SEQ ID NO:17) | 5 | 10 |
| TEDK | KYCNGKRVCVCR—NH$_2$ (SEQ ID NO:18) | 5 | 5 |
| TEDP | PYCNGKRVCVCR—NH$_2$ (SEQ ID NO:19) | 5 | 5 |
| TEDS | SYCNGKRVCVCR—NH$_2$ (SEQ ID NO:20) | 10 | 50 |
| TEDA | AYCNGKRVCVCR—NH$_2$ (SEQ ID NO:21) | 10 | 10 |
| TEDD | DYCNGKRVCVCR—NH$_2$ (SEQ ID NO:22) | 10 | 50 |
| TEDL | LYCNGKRVCVCR—NH$_2$ (SEQ ID NO:23) | 5 | 5 |
| TEDW | WYCNGKRVCVCR—NH$_2$ (SEQ ID NO:24) | 20 | 20 |

TABLE 4

Addition of an amino acid to N-terminal of the TEDF peptide

| Name | Amino acid sequence | MIC(μg/ml) S. aureus | C. albicans |
|---|---|---|---|
| TEDF | FYCNGKRVCVCR—NH₂ (SEQ ID NO:17) | 5 | 10 |
| TEDFK | FKYCNGKRVCVCR—NH₂ (SEQ ID NO:25) | 5 | 3 |
| TEDFF | FFYCNGKRVCVCR—NH₂ (SEQ ID NO:26) | 5 | 3 |
| TEDFP | FPYCNGKRVCVCR—NH₂ (SEQ ID NO:27) | >500 | >500 |
| TEDFS | SFYCNGKRVCVCR—NH₂ (SEQ ID NO:28) | 50 | 10 |
| TEDFY | YFYCNGKRVCVCR—NH₂ (SEQ ID NO:29) | 50 | 100 |
| TEDFD | DFYCNGKRVCVCR—NH₂ (SEQ ID NO:30) | >500 | >500 |
| TEDFL | LFYCNGKRVCVCR—NH₂ (SEQ ID NO:31) | 30 | 100 |
| TEDFW | WFYCNGKRVCVCR—NH₂ (SEQ ID NO:32) | 1 | 10 |

TABLE 5

Modification of the TEDFK peptide

| Name | Amino acid sequence | MIC(μg/ml) against C. albicans |
|---|---|---|
| TEDFK | KFYCNGKRVCVCR—NH₂ (SEQ ID NO:25) | 3 |
| TEDFK-1 | KFYCNKRVCVCR—NH₂ (SEQ ID NO:33) | 5 |
| TEDFK-2 | KFYCNGRVCVCR—NH₂ (SEQ ID NO:34) | 5 |
| TEDFK-3 | KFYCNPKRVCVCR—NH₂ (SEQ ID NO:35) | 5 |
| TEDFK-4 | KFYCNLKRVCVCR—NH₂ (SEQ ID NO:36) | 5 |
| TEDFK-5 | KFYCNKKRVCVCR—NH₂ (SEQ ID NO:37) | 5 |
| TEDFK-6 | KFYCVGKRVCVCR—NH₂ (SEQ ID NO:38) | 5 |
| TEDFK-7 | KFYCKGKRVCVCR—NH₂ (SEQ ID NO:39) | 3 |
| TEDFK-8 | KFYCNGKRVCVCR—NH₂ (SEQ ID NO:40) | 5 |
| TEDFK-9 | KFYCNPGPVCVCR—NH₂ (SEQ ID NO:41) | 20 |
| TEDFK-10 | KFYCNGKRVCVCL—NH₂ (SEQ ID NO:42) | 5 |
| TEDFK-11 | KFYCNGKRVCVCD—NH₂ (SEQ ID NO:43) | 5 |

TABLE 6

Substitution of Cys in the TEDFK peptide with aminoisobutyric acid(Aib)

| Name | Amino acid sequence | MIC(μg/ml) against C. albicans |
|---|---|---|
| TEDFK | KFYCNGKRVCVCR—NH₂ (SEQ ID NO:25) | 3 |
| TEDFK-1A | KFY(Aib)NGKRVCVCR—NH₂ (SEQ ID NO:44) | 1 to 3 |
| TEDFK-2A | KFYCNGKRV(Aib)VCR—NH₂ (SEQ ID NO:45) | 5 |
| TEDFK-3A | KFYCNGKRVCV(Aib)R—NH₂ (SEQ ID NO:46) | 20 |
| TEDFK-1,2A | KFY(Aib)NGKRV(Aib)VCR—NH₂ (SEQ ID NO:47) | 20 |

As can be seen in Tables 2 to 6, it was clearly demonstrated that peptide TED, TEDF, TEDFK and derivatives thereofs of the present invention possess excellent antibacterial and/or antifungal activities.

EXAMPLE 3

Comparison of Antifungal Activity of the Synthesized Peptides and Ketoconazole

Derivatives of peptide TEDFK whose amino acid sequences are disclosed in Tables 5 and 6, were subjected to a comparison of the antifungal activity with a commercially available antifungal drug, Ketoconazole (Janssen Foundation, Belgium).

TABLE 7

Antifungal activity of the synthesized peptides and Ketoconazole

| Name | MIC(μg/ml) against C. albicans |
|---|---|
| Ketoconazole | 6 |
| TEDFK-2 | 6 |
| TEDFK-3 | 6 |
| TEDFK-5 | 3 |
| TEDFK-6 | 6 |
| TEDFK-7 | 3 |
| TEDFK-8 | 6 |
| TEDFK-9 | 12 |
| TEDFK-10 | 6 |
| TEDFK-11 | 6 |
| TEDFK-1A | 2 |
| TEDFK-2A | 6 |
| TEDFK-3A | 12 |

As can be seen in Table 7, it was determined that some of TEDFK peptide derivatives exhibit much higher antifungal activity than that of Ketoconazole.

EXAMPLE 4

Antibiotic Activity of TEDFK Peptide Analogues (I)

Further modifications of a peptide TEDFK were made by employing addition, deletion and substitution of amino acids, to prepare a number of peptide derivatives which can be classified as 3 groups fallen within the general formula (II), (III) and (IV), respectively. Antibacterial and antifungal activities for the peptide derivatives were determined analogously as in Example 2(see: Tables 8, 9 and 10).

TABLE 8

Antibiotic activity of TEDFK peptide derivatives of group 1

| Name | Amino acid sequence | MIC(µg/ml) S. aureus | C. albicans |
|---|---|---|---|
| TEDFK | KFYCNGKRVCVCR—NH$_2$ (SEQ ID NO:25) | 6.25 | 6.25 |
| M1 | KKYCNGKRVCVCR—NH$_2$ (SEQ ID NO:48) | 3.16 | 3.12 |
| M2 | KPYCNGKRVCVCR—NH$_2$ (SEQ ID NO:49) | 6.35 | 6.25 |
| M3 | FKYCNGKRVCVCR—NH$_2$ (SEQ ID NO:50) | 12.7 | 12.5 |
| M4 | KKYCNXRVCVCR—NH$_2$ (SEQ ID NO:51) | 3.16 | 3.12 |
| M5 | KKYCNKKCVCK—NH$_2$ (SEQ ID NO:52) | 3.16 | 3.12 |
| M6 | KKYCNKKCVCK—NH$_2$ (SEQ ID NO:53) | 3.16 | 3.12 |
| M8 | KFY(Aib)KKVCVCK—NH$_2$ (SEQ ID NO:54) | 3.16 | 3.12 |
| M9 | KFYINGKRVCVCR—NH$_2$ (SEQ ID NO:55) | 3.16 | 3.12 |
| M10 | KFYSNGKRVCVCR—NH$_2$ (SEQ ID NO:56) | 6.35 | 6.25 |
| M11 | KFYCNGKRVSVCR—NH$_2$ (SEQ ID NO:57) | 6.35 | 6.25 |
| M12 | KFYCNGKRVCVnLR—NH$_2$ (SEQ ID NO:58) | 6.35 | 6.25 |
| M13 | KFYCNGKRICICR—NH$_2$ (SEQ ID NO:59) | 6.35 | 6.25 |
| M14 | KFY(Aib)NGKRVIVCR—NH$_2$ (SEQ ID NO:60) | 12.7 | 12.5 |
| M15 | YCNGKRVCVCRKK—NH$_2$ (SEQ ID NO:61) | 6.35 | 6.25 |
| M16 | KYCNGKRVCVCRK—NH$_2$ (SEQ ID NO:62) | 6.35 | 6.25 |
| M17 | KFY(Aib)KGKRVCVCR—NH$_2$ (SEQ ID NO:63) | 6.35 | 6.25 |
| M18 | KFYCDGKRVCVCR—NH$_2$ (SEQ ID NO:64) | 12.7 | 12.5 |
| M19 | KFY(Aib)NGKKVFVFK—NH$_2$ (SEQ ID NO:65) | 6.35 | 6.25 |
| M21 | KIIINKKICICK—NH$_2$ (SEQ ID NO:66) | 3.16 | 3.12 |
| M25 | KFYCNGKRV(Aib)VCK—NH$_2$ (SEQ ID NO:67) | 6.35 | 6.25 |
| M26 | KWYCNGKRVCVCR—NH$_2$ (SEQ ID NO:68) | 6.35 | 6.25 |
| M27 | KFYCNGKRVWVCR—NH$_2$ (SEQ ID NO:69) | 6.35 | 6.25 |
| M28 | KFYCNGKRVCVWR—NH$_2$ (SEQ ID NO:70) | 12.7 | 12.5 |
| M29 | WFYCNGKRVCVCR—NH$_2$ (SEQ ID NO:71) | 30 | 25 |
| M30 | KFYCNWKRVCVCR—NH$_2$ (SEQ ID NO:72) | 12.7 | 12.5 |
| M31 | KFYCNGKRVCVCW—NH$_2$ (SEQ ID NO:73) | 12.7 | 12.5 |

*nL: norleucine, Aib: aminoisobutyric acid

TABLE 9

Antibiotic activity of TEDFK peptide derivatives of group 2

| Name | Amino acid sequence | MIC(µg/ml) S. aureus | C. albicans |
|---|---|---|---|
| TEDFK | KFYCNGKRVCVCR—NH$_2$ (SEQ ID NO:25) | 6.25 | 6.25 |
| M20 | KFY(Aib)KKVFVFK—NH$_2$ (SEQ ID NO:74) | 6.35 | 6.25 |
| M22 | KKYIKVFVFK—NH$_2$ (SEQ ID NO:75) | 3.16 | 3.12 |
| M23 | KYIKKVFVFK—NH$_2$ (SEQ ID NO:76) | 3.16 | 3.12 |
| M24 | KKKIKKVFVFK—NH$_2$ (SEQ ID NO:77) | 3.16 | 3.12 |
| M35 | KKYIKKYIKK—NH$_2$ (SEQ ID NO:78) | 12.7 | 12.5 |
| M36 | KVFVFKFVFVK—NH$_2$ (SEQ ID NO:79) | 6.25 | 6.25 |

*Aib: aminoisobutyric acid

As can be seen in Table 10, it was determined that TEDFK peptide derivatives of group 3 possess excellent antifungal activity.

TABLE 10

Antifungal activity of TEDFK peptide derivatives of group 3

| Name | Amino acid sequence | MIC(µg/ml) against C. albicans |
|---|---|---|
| TEDFK | KFYCNGKRVCVCR—NH$_2$ (SEQ ID NO:25) | 6.25 |
| M32 | KKKKYIVFVFK—NH$_2$ (SEQ ID NO:80) | 3.12 |
| M33 | KKYIVFVFK—NH$_2$ (SEQ ID NO:81) | 3.12 |
| M34 | KKYIVFVFK—NH$_2$ (SEQ ID NO:82) | 3.12 |
| M37 | KYIVFVFK—NH$_2$ (SEQ ID NO:83) | 3.12 |

EXAMPLE 5

Antibiotic Activity of TEDFK Peptide Analogues (II)

Enantiomers and retro-inversoes of TEDFK were prepared heir antibiotic activities were determined analogously Example 2. In addition, derivatives of M22 peptide in Table 9 where at most 3 neighboring amino acids located in each of N- and/or C-terminals, or at most 2 neighboring amino acids in the mid-part of the peptide, were substituted with D-form amino acids, were prepared, and their antibacterial and antifungal activities were also determined (see: Table 11).

TABLE 11

Antibiotic activity of TEDFK peptide derivatives*

| Name | Amino acid sequence | MIC(μg/ml) S. aureus | C. albicans |
|---|---|---|---|
| TEDFK | KFYCNGKRVCVCR—NH$_2$ (SEQ ID NO:25) | 6.25 | 6.25 |
| Enantiomer of TEDFK | kfycngkrvcvcr-NH$_2$ (SEQ ID NO:84) | 6.35 | 6.35 |
| Retro-inverso of TEDFK | rcvcvrkgncyfk-NH$_2$ (SEQ ID NO:85) | 6.25 | 6.25 |
| M22 | KKYIKKVFVFK—NH$_2$ (SEQ ID NO:75) | 3.16 | 3.12 |
| M22-1 | kKYIKKVFVFK—NH$_2$ | 3.15 | 3.12 |
| M22-2 | kkYIKKVFVFK—NH$_2$ | 3.15 | 3.12 |
| M22-3 | kkyIKKVFVFK—NH$_2$ | 3.16 | 3.12 |
| M22-4 | KKYIKKVFVFk—NH$_2$ | 3.17 | 3.11 |
| M22-5 | KKYIKKVFVfk—NH$_2$ | 3.12 | 3.12 |
| M22-6 | KKYIKKVFvfk—NH$_2$ | 3.13 | 3.15 |
| M22-7 | KKYIKKVFvfk—NH$_2$ | 3.11 | 3.12 |
| M22-8 | kkYIKKVFVFk—NH$_2$ | 3.16 | 3.12 |
| M22-9 | kkyIKKVFVFk—NH$_2$ | 3.15 | 3.11 |
| M22-10 | kKYIKKVFVfk—NH$_2$ | 3.17 | 3.15 |
| M22-11 | kkYIKKVFVfk—NH$_2$ | 3.16 | 3.14 |
| M22-12 | kkyIKKVFVfk—NH$_2$ | 3.15 | 3.15 |
| M22-13 | kKYIKKVFvfk—NH$_2$ | 3.18 | 3.15 |
| M22-14 | kkYIKKVFvfk—NH$_2$ | 3.13 | 3.11 |
| M22-15 | kkyIKKVFvfk—NH$_2$ | 3.12 | 3.12 |
| M22-16 | KkYIKKVFVFK—NH$_2$ | 3.15 | 3.16 |
| M22-17 | KKyIKKVFVFK—NH$_2$ | 3.15 | 3.12 |
| M22-18 | KKYiKKVFVFK—NH$_2$ | 3.16 | 3.15 |
| M22-19 | KKYIkKVFVFK—NH$_2$ | 3.15 | 3.14 |
| M22-20 | KKYIKkVFVFK—NH$_2$ | 3.16 | 3.12 |
| M22-21 | KKYIKKvFVFK—NH$_2$ | 3.17 | 3.15 |
| M22-22 | KKYIKKVfVFK—NH$_2$ | 3.15 | 3.12 |
| M22-23 | KKYIKKVFvFK—NH$_2$ | 3.16 | 3.17 |
| M22-24 | KKYIKKVFVfK—NH$_2$ | 3.14 | 3.11 |
| M22-25 | KkyIKKVFVFK—NH$_2$ | 3.15 | 3.12 |
| M22-26 | KKyIKKVFVFK—NH$_2$ | 3.16 | 3.15 |
| M22-27 | KKYIkkVFVFK—NH$_2$ | 3.17 | 3.11 |
| M22-28 | KKYIkkVFVFK—NH$_2$ | 3.15 | 3.12 |
| M22-29 | KKYIKkvFVFK—NH$_2$ | 3.15 | 3.11 |
| M22-30 | KKYIKKvfVFK—NH$_2$ | 3.17 | 3.12 |
| M22-31 | KKYIKKVfvFK—NH$_2$ | 3.16 | 3.15 |
| M22-32 | KKYIKKVFvfK—NH$_2$ | 3.15 | 3.12 |

*small letters represent D-form amino acids.

As shown in Table 11, it was proved that enantiomers and retro-inversoes of TEDFK, and derivatives of M22 peptide possess both antibacterial and antifungal activities to the level of TEDFK and M22 peptide, respectively.

From the above results, it was determined that the analogues, i.e., enantiomers, retro-inversoes and derivatives where at most 3 neighboring amino acids located in each of N- and/or C-terminals, or at most 2 neighboring amino acids in the mid-part of the peptides, are substituted with D-form amino acids, have similar activities to those of the parent peptides of the present invention, which is correlated with the previous reports that antibiotic peptides have no stereo-specificity for the targeted membrane since the peptides interact the membrane without specific binding with chiral receptor or enzyme (see: Bessalle, R. et al., FEBS Lett., 274:151–155(1990); Wade, D. et al., Proc. Natl. Acad. Sci., USA, 87:4761–4765(1990); Matsuzaki, K. et al., Biochemistry, 34:3423–3429(1995); Merrifield, R. B. et al., Proc. Natl. Acad. Sci., USA, 92:3449–3453(1995); Krause, E. et al., Anal. Chem., 67:252–258(1995)).

EXAMPLE 6

Cytotoxicity

To examine whether the peptides synthesized in the invention cause cell lysis or not, red blood cells were first obtained by the centrifugation of 3ml of human blood, rinsed with PBS (phosphate buffered saline) solution three times and diluted with the same solution to have 20 ml in total. To 190 μl of the red blood cell-containing solution thus prepared, was added 10 μl of peptide solution prior to the incubation at 37° C. for 30 min. After incubation, centrifugation followed to obtain supernatant. Then, a level (%) of cell lysis caused by peptides was determined by the examination of absorbance at 576 nm (see: Table 12). At this moment, TEDFK, TEDFK-1A, M5, M6, M19, M22 and M32 were chosen as peptide fragments of Tenecin, and an antibiotic peptide KLK (see: Natori, S. et al., J. Biochem., 117(6):1312–1316(1995)) and a commercially available antibiotic, Amphotericin B(Sigma, USA) known to lyse a red blood cell were employed as controls, respectively.

TABLE 12

Lysis of red blood cell(%)

| Peptide concentration (μg/ml) | Cell lysis(%) | | | | | | | | |
|---|---|---|---|---|---|---|---|---|---|
| | TEDFK | TEDFK-1A | M5 | M6 | M19 | M22 | M32 | KLK* | Amphotericin B |
| 0.078 | 0 | 0 | 0 | 0 | 0 | 0 | 0 | 0 | 0 |
| 0.625 | 0 | 0 | 0 | 0 | 0 | 0 | 0 | 0 | 8.06 |
| 7.8 | 0 | 0 | 0 | 0 | 0 | 0 | 0 | 0 | 100 |
| 31.2 | 0 | 0 | 0 | 0 | 0 | 0 | 0 | 9.6 | 100 |
| 62.5 | 0 | 0 | 0 | 0 | 0 | 0 | 0 | 78.6 | 100 |
| 125 | 0 | 0 | 0 | 0 | 0 | 0 | 0 | 89.9 | 100 |
| 250 | 0 | 0 | 0 | 0 | 0 | 0 | 0 | 100 | 100 |
| 500 | 0 | 0 | 0 | 0 | 0 | 0 | 0 | 100 | 100 |
| 1000 | 0 | 0 | 0 | 0 | 0 | 0 | 0 | 100 | 100 |
| 5000 | 0.28 | 0 | 30.6 | 13.3 | 0 | 0 | 0 | 100 | 100 |

*KLK is a peptide whose amino acid sequence is KLKLLLLLKLK—NH$_2$(SEQ ID NO:86).

As can be seen in Table 12 above, it was clearly determined that the peptides of the invention do not cause cell lysis, which was a surprising finding to guarantee the safety of the antibiotic peptides of the invention, since both of controls including a commercially available antibiotic such as Amphotericin B, cause cell lysis which is one of serious untoward effects in a human body administered with the antibiotics.

As clearly illustrated and demonstrated above, the present invention provides novel antibiotic peptides which possess superior antibacterial and/or antifungal activities causing no untoward effects such as cell lysis, and to pharmaceutical compositions containing said peptides as active ingredients.

---

What is claimed is:

1. Acid- or amide-form peptides which possess both antibacterial and antifungal activities, which are represented by the general formula(II), including enantiomers, retro-inversoes and derivatives where at most 3 neighboring amino acids located in each of N- and/or C-terminals, or at most 2 neighboring amino acids in the mid-part of the peptides, are substituted with D-form amino acids, respectively:

$$\beta^1\ \beta^2\ \beta^3\ \beta^4\ \beta^5\ \beta^6\ \beta^7\ \beta^8\ \beta^9\ \beta^{10} \qquad (II)$$

wherein, $\beta^1$ is vacant, or 1 or 2 basic amino acids;

$\beta^2$ is vacant, or 1 or 2 hydrophobic or basic amino acids(provided that $\beta^1$ is vacant and $\beta^2$ is 1 residue of amino acid, Pro and Tyr are excluded);

$\beta^3$ is 2 amino acids selected from the group consisting of hydrophobic amino acids and Cys;

$\beta^4$ is 1 or 2 amino acids(provided that $\beta^4$ is 1 residue of amino acid, Pro and acidic amino acids are excluded; and, provided that $\beta^4$ is 2 amino acids, both of which can not be acidic amino acids);

$\beta^5$ is 1 or 2 basic amino acids;

$\beta^6$ is vacant, or a hydrophobic amino acid;

$\beta^7$ is an amino acid selected from the group consisting of hydrophobic aromatic and aliphatic amino acids, Cys and Ser;

$\beta^8$ is a hydrophobic amino acid;

$\beta^9$ is an amino acid selected from the group consisting of hydrophobic aromatic and aliphatic amino acids, Cys and Ser (provided that $\beta^7$ is a hydrophobic aliphatic amino acid or Ser, $\beta^9$ can be a hydrophobic aromatic amino acid or Cys); and, $\beta^{10}$ is 1 or 2 basic amino acids.

2. A pharmaceutical composition which shows both antibacterial and antifungal activities, which contains at least one of peptides in claim 1 as active ingredient and pharmaceutically acceptable carriers.

* * * * *

SEQUENCE LISTING ( 1 ) GENERAL INFORMATION:

( i i i ) NUMBER OF SEQUENCES: 86

( 2 ) INFORMATION FOR SEQ ID NO:1:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: unknown ( i i ) MOLECULE TYPE: peptide ( v i ) ORIGINAL SOURCE:
        ( A ) ORGANISM: Tenebrio molitor
        ( D ) DEVELOPMENTAL STAGE: Larva ( v i i ) IMMEDIATE SOURCE:
        ( B ) CLONE: Tenecin ( x i ) SEQUENCE DESCRIPTION: SEQ ID NO:1:

```
Val Thr Cys Asp Ile Leu Ser Val Glu Ala Lys Gly Val Lys Leu Asn
 1               5                  10                  15
Asp Ala Ala Cys Ala Ala His Cys Leu Phe Arg Gly Arg Ser Gly Gly
            20                  25                  30
Tyr Cys Asn Gly Lys Arg Val Cys Val Cys Arg
        35                  40
```

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TEA ( x i ) SEQUENCE DESCRIPTION: SEQ ID NO:2:

```
Arg Phe Leu Cys His His Ala Ala Cys Ala Ala Asp
 1               5                  10
```

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TEB -continued (x i) SEQUENCE DESCRIPTION: SEQ ID NO:3:

Gly Gly Ser Arg Gly Arg Phe Leu Cys His Ala Ala Cys Ala Ala Asp
1               5                   10                  15

Asn (2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (i i) MOLECULE TYPE: peptide (v i i) IMMEDIATE SOURCE:
        (B) CLONE: TEC (x i) SEQUENCE DESCRIPTION: SEQ ID NO:4:

Leu Lys Val Gly Lys Ala Glu Val Ser Leu Ile Asp Cys Thr Val
1               5                   10                  15

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (i i) MOLECULE TYPE: peptide (v i i) IMMEDIATE SOURCE:
        (B) CLONE: TED (x i) SEQUENCE DESCRIPTION: SEQ ID NO:5:

Arg Cys Val Cys Val Arg Lys Gly Asn Cys Tyr
1               5                   10

(2) INFORMATION FOR SEQ ID NO:6:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (i i) MOLECULE TYPE: peptide (v i i) IMMEDIATE SOURCE:
        (B) CLONE: TEO (x i) SEQUENCE DESCRIPTION: SEQ ID NO:6:

Leu Cys His Ala Ala Cys Ala Ala Asp Asn Leu Lys Val Gly Lys Ala
1               5                   10                  15

Glu Val Ser Leu
                20

(2) INFORMATION FOR SEQ ID NO:7:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (i i) MOLECULE TYPE: peptide (v i i) IMMEDIATE SOURCE:
        (B) CLONE: TEQ ( x i ) SEQUENCE DESCRIPTION: SEQ ID NO:7:

Arg Cys Val Cys Val Arg Lys Gly Asn Cys Tyr Gly Gly Gly Leu Lys
1               5                   10                  15
Val Gly Lys Ala Glu Val Ser Leu
            20

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TED11

( x i ) SEQUENCE DESCRIPTION: SEQ ID NO:8:

Arg Cys Val Cys Val Arg Lys Gly
1               5

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TED12

( x i ) SEQUENCE DESCRIPTION: SEQ ID NO:9:

Arg Cys Val Cys Val Arg Lys Gly Lys
1               5

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TED13

( x i ) SEQUENCE DESCRIPTION: SEQ ID NO:10:

Arg Cys Val Cys Val Arg Lys Gly Asn
1               5

( 2 ) INFORMATION FOR SEQ ID NO:11:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TED14

( x i ) SEQUENCE DESCRIPTION: SEQ ID NO:11:

Arg Cys Val Cys Val Arg Lys Gly Asn Ser
1               5                   10

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TED15

( x i ) SEQUENCE DESCRIPTION: SEQ ID NO:12:

Arg Cys Val Cys Val Arg Lys Gly Asn Cys
1               5                   10

( 2 ) INFORMATION FOR SEQ ID NO:13:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TED16

( x i ) SEQUENCE DESCRIPTION: SEQ ID NO:13:

Arg Cys Val Cys Val Arg Lys Gly Asn Cys Phe
1               5                   10

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TED17

( x i ) SEQUENCE DESCRIPTION: SEQ ID NO:14:

Arg Cys Val Cys Val Arg Lys Gly Asn Cys Leu
1               5                   10

( 2 ) INFORMATION FOR SEQ ID NO:15:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TED18

( x i ) SEQUENCE DESCRIPTION: SEQ ID NO:15:

Arg Cys Val Cys Val Arg Lys Gly Asn Cys Lys
1               5                   10

( 2 ) INFORMATION FOR SEQ ID NO:16:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TED19

( x i ) SEQUENCE DESCRIPTION: SEQ ID NO:16:

Arg Cys Val Cys Val Arg Lys Gly Asn Ser Trp
1               5                   10

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TEDF ( x i ) SEQUENCE DESCRIPTION: SEQ ID NO:17:

Arg Cys Val Cys Val Arg Lys Gly Asn Cys Tyr Phe
1               5                   10

( 2 ) INFORMATION FOR SEQ ID NO:18:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TEDK ( x i ) SEQUENCE DESCRIPTION: SEQ ID NO:18:

Arg Cys Val Cys Val Arg Lys Gly Asn Cys Tyr Lys
1               5                   10

( 2 ) INFORMATION FOR SEQ ID NO:19:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TEDP ( x i ) SEQUENCE DESCRIPTION: SEQ ID NO:19:

Arg Cys Val Cys Val Arg Lys Gly Asn Cys Tyr Pro
1               5                   10

( 2 ) INFORMATION FOR SEQ ID NO:20:

( i ) SEQUENCE CHARACTERISTICS:
  ( A ) LENGTH: 12 amino acids
  ( B ) TYPE: amino acid
  ( C ) STRANDEDNESS: unknown
  ( D ) TOPOLOGY: unknown ( i i ) MOLECULE TYPE: peptide ( v i i ) IMMEDIATE SOURCE:
  ( B ) CLONE: TEDS ( x i ) SEQUENCE DESCRIPTION: SEQ ID NO:20:

Arg Cys Val Cys Val Arg Lys Gly Asn Cys Tyr Ser
 1               5                   10

( 2 ) INFORMATION FOR SEQ ID NO:21:

( i ) SEQUENCE CHARACTERISTICS:
    ( A ) LENGTH: 12 amino acids
    ( B ) TYPE: amino acid
    ( C ) STRANDEDNESS: unknown
    ( D ) TOPOLOGY: unknown ( i i ) MOLECULE TYPE: peptide ( v i i ) IMMEDIATE SOURCE:
    ( B ) CLONE: TEDA ( x i ) SEQUENCE DESCRIPTION: SEQ ID NO:21:

Arg Cys Val Cys Val Arg Lys Gly Asn Cys Tyr Ala
 1               5                   10

( 2 ) INFORMATION FOR SEQ ID NO:22:

( i ) SEQUENCE CHARACTERISTICS:
    ( A ) LENGTH: 12 amino acids
    ( B ) TYPE: amino acid
    ( C ) STRANDEDNESS: unknown
    ( D ) TOPOLOGY: unknown ( i i ) MOLECULE TYPE: peptide ( v i i ) IMMEDIATE SOURCE:
    ( B ) CLONE: TEDD ( x i ) SEQUENCE DESCRIPTION: SEQ ID NO:22:

Arg Cys Val Cys Val Arg Lys Gly Asn Cys Tyr Asp
 1               5                   10

( 2 ) INFORMATION FOR SEQ ID NO:23:

( i ) SEQUENCE CHARACTERISTICS:
    ( A ) LENGTH: 12 amino acids
    ( B ) TYPE: amino acid
    ( C ) STRANDEDNESS: unknown
    ( D ) TOPOLOGY: unknown ( i i ) MOLECULE TYPE: peptide ( v i i ) IMMEDIATE SOURCE:
    ( B ) CLONE: TEDL ( x i ) SEQUENCE DESCRIPTION: SEQ ID NO:23:

Arg Cys Val Cys Val Arg Lys Gly Asn Cys Tyr Leu
 1               5                   10

( 2 ) INFORMATION FOR SEQ ID NO:24:

( i ) SEQUENCE CHARACTERISTICS:
    ( A ) LENGTH: 12 amino acids
    ( B ) TYPE: amino acid
    ( C ) STRANDEDNESS: unknown (D) TOPOLOGY: unknown (i i) MOLECULE TYPE: peptide (v i i) IMMEDIATE SOURCE:
  (B) CLONE: TEDW (x i) SEQUENCE DESCRIPTION: SEQ ID NO:24:

Arg Cys Val Cys Val Arg Lys Gly Asn Cys Tyr Trp
1               5                   10

(2) INFORMATION FOR SEQ ID NO:25:

(i) SEQUENCE CHARACTERISTICS:
    (A) LENGTH: 13 amino acids
    (B) TYPE: amino acid
    (C) STRANDEDNESS: unknown
    (D) TOPOLOGY: unknown (i i) MOLECULE TYPE: peptide (v i i) IMMEDIATE SOURCE:
    (B) CLONE: TEDFK (x i) SEQUENCE DESCRIPTION: SEQ ID NO:25:

Arg Cys Val Cys Val Arg Lys Gly Asn Cys Tyr Phe Lys
1               5                   10

(2) INFORMATION FOR SEQ ID NO:26:

(i) SEQUENCE CHARACTERISTICS:
    (A) LENGTH: 13 amino acids
    (B) TYPE: amino acid
    (C) STRANDEDNESS: unknown
    (D) TOPOLOGY: unknown (i i) MOLECULE TYPE: peptide (v i i) IMMEDIATE SOURCE:
    (B) CLONE: TEDFF (x i) SEQUENCE DESCRIPTION: SEQ ID NO:26:

Arg Cys Val Cys Val Arg Lys Gly Asn Cys Tyr Phe Phe
1               5                   10

(2) INFORMATION FOR SEQ ID NO:27:

(i) SEQUENCE CHARACTERISTICS:
    (A) LENGTH: 13 amino acids
    (B) TYPE: amino acid
    (C) STRANDEDNESS: unknown
    (D) TOPOLOGY: unknown (i i) MOLECULE TYPE: peptide (v i i) IMMEDIATE SOURCE:
    (B) CLONE: TEDFP (x i) SEQUENCE DESCRIPTION: SEQ ID NO:27:

Arg Cys Val Cys Val Arg Lys Gly Asn Cys Tyr Phe Pro
1               5                   10

(2) INFORMATION FOR SEQ ID NO:28:

(i) SEQUENCE CHARACTERISTICS:
    (A) LENGTH: 13 amino acids
    (B) TYPE: amino acid
    (C) STRANDEDNESS: unknown
    (D) TOPOLOGY: unknown (i i) MOLECULE TYPE: peptide

```
        ( v i i ) IMMEDIATE SOURCE:
                ( B ) CLONE: TEDFS ( x i ) SEQUENCE DESCRIPTION: SEQ ID NO:28:

Arg  Cys  Val  Cys  Val  Arg  Lys  Gly  Asn  Cys  Tyr  Phe  Ser
 1                   5                        1 0
```

( 2 ) INFORMATION FOR SEQ ID NO:29:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TEDFY ( x i ) SEQUENCE DESCRIPTION: SEQ ID NO:29:

```
Arg  Cys  Val  Cys  Val  Arg  Lys  Gly  Asn  Cys  Tyr  Phe  Tyr
 1                   5                        1 0
```

( 2 ) INFORMATION FOR SEQ ID NO:30:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TEDFD ( x i ) SEQUENCE DESCRIPTION: SEQ ID NO:30:

```
Arg  Cys  Val  Cys  Val  Arg  Lys  Gly  Asn  Cys  Tyr  Phe  Asp
 1                   5                        1 0
```

( 2 ) INFORMATION FOR SEQ ID NO:31:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TEDFL ( x i ) SEQUENCE DESCRIPTION: SEQ ID NO:31:

```
Arg  Cys  Val  Cys  Val  Arg  Lys  Gly  Asn  Cys  Tyr  Phe  Leu
 1                   5                        1 0
```

( 2 ) INFORMATION FOR SEQ ID NO:32:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TEDFW ( x i ) SEQUENCE DESCRIPTION: SEQ ID NO:32:

Arg Cys Val Cys Val Arg Lys Gly Asn Cys Tyr Phe Trp
1               5                   10

(2) INFORMATION FOR SEQ ID NO:33:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (vii) IMMEDIATE SOURCE:
        (B) CLONE: TEDFK-1

(xi) SEQUENCE DESCRIPTION: SEQ ID NO:33:

Arg Cys Val Cys Val Arg Lys Asn Cys Tyr Phe Lys
1               5                   10

(2) INFORMATION FOR SEQ ID NO:34:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (vii) IMMEDIATE SOURCE:
        (B) CLONE: TEDFK-2

(xi) SEQUENCE DESCRIPTION: SEQ ID NO:34:

Arg Cys Val Cys Val Arg Gly Asn Cys Tyr Phe Lys
1               5                   10

(2) INFORMATION FOR SEQ ID NO:35:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (vii) IMMEDIATE SOURCE:
        (B) CLONE: TEDFK-3

(xi) SEQUENCE DESCRIPTION: SEQ ID NO:35:

Arg Cys Val Cys Val Arg Lys Pro Asn Cys Tyr Phe Lys
1               5                   10

(2) INFORMATION FOR SEQ ID NO:36:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (vii) IMMEDIATE SOURCE:
        (B) CLONE: TEDFK-4

(xi) SEQUENCE DESCRIPTION: SEQ ID NO:36:

Arg Cys Val Cys Val Arg Lys Leu Asn Cys Tyr Phe Lys
1               5                   10

( 2 ) INFORMATION FOR SEQ ID NO:37:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TEDFK-5

( x i ) SEQUENCE DESCRIPTION: SEQ ID NO:37:

```
Arg  Cys  Val  Cys  Val  Arg  Lys  Lys  Asn  Cys  Tyr  Phe  Lys
 1              5                        10
```

( 2 ) INFORMATION FOR SEQ ID NO:38:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TEDFK-6

( x i ) SEQUENCE DESCRIPTION: SEQ ID NO:38:

```
Arg  Cys  Val  Cys  Val  Arg  Lys  Gly  Val  Cys  Tyr  Phe  Lys
 1              5                        10
```

( 2 ) INFORMATION FOR SEQ ID NO:39:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TEDFK-7

( x i ) SEQUENCE DESCRIPTION: SEQ ID NO:39:

```
Arg  Cys  Val  Cys  Val  Arg  Lys  Gly  Lys  Cys  Tyr  Phe  Lys
 1              5                        10
```

( 2 ) INFORMATION FOR SEQ ID NO:40:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: TEDFK-8

( x i ) SEQUENCE DESCRIPTION: SEQ ID NO:40:

```
Arg  Cys  Val  Cys  Val  Lys  Gly  Asn  Cys  Tyr  Phe  Lys
 1              5                   10
```

( 2 ) INFORMATION FOR SEQ ID NO:41:

( i ) SEQUENCE CHARACTERISTICS:

( A ) LENGTH: 13 amino acids
( B ) TYPE: amino acid
( C ) STRANDEDNESS: unknown
( D ) TOPOLOGY: unknown ( i i ) MOLECULE TYPE: peptide ( v i i ) IMMEDIATE SOURCE:
( B ) CLONE: TEDFK-9

( x i ) SEQUENCE DESCRIPTION: SEQ ID NO:41:

```
Arg Cys Val Cys Val Pro Gly Pro Asn Cys Tyr Phe Lys
 1               5                   1 0
```

( 2 ) INFORMATION FOR SEQ ID NO:42:

( i ) SEQUENCE CHARACTERISTICS:
( A ) LENGTH: 13 amino acids
( B ) TYPE: amino acid
( C ) STRANDEDNESS: unknown
( D ) TOPOLOGY: unknown ( i i ) MOLECULE TYPE: peptide ( v i i ) IMMEDIATE SOURCE:
( B ) CLONE: TEDFK-10

( x i ) SEQUENCE DESCRIPTION: SEQ ID NO:42:

```
Leu Cys Val Cys Val Arg Lys Gly Asn Cys Tyr Phe Lys
 1               5                   1 0
```

( 2 ) INFORMATION FOR SEQ ID NO:43:

( i ) SEQUENCE CHARACTERISTICS:
( A ) LENGTH: 13 amino acids
( B ) TYPE: amino acid
( C ) STRANDEDNESS: unknown
( D ) TOPOLOGY: unknown ( i i ) MOLECULE TYPE: peptide ( v i i ) IMMEDIATE SOURCE:
( B ) CLONE: TEDFK-11

( x i ) SEQUENCE DESCRIPTION: SEQ ID NO:43:

```
Asp Cys Val Cys Val Arg Lys Gly Asn Cys Tyr Phe Lys
 1               5                   1 0
```

( 2 ) INFORMATION FOR SEQ ID NO:44:

( i ) SEQUENCE CHARACTERISTICS:
( A ) LENGTH: 13 amino acids
( B ) TYPE: amino acid
( C ) STRANDEDNESS: unknown
( D ) TOPOLOGY: unknown ( i i ) MOLECULE TYPE: peptide ( v i i ) IMMEDIATE SOURCE:
( B ) CLONE: TEDFK-1A ( i x ) FEATURE: Amino acid 10 is aminoisobutyric acid (Aib)

( x i ) SEQUENCE DESCRIPTION: SEQ ID NO:44:

```
Arg Cys Val Cys Val Arg Lys Gly Asn Xaa Tyr Phe Lys
 1               5                   1 0
```

( 2 ) INFORMATION FOR SEQ ID NO:45:

( i ) SEQUENCE CHARACTERISTICS:
( A ) LENGTH: 13 amino acids
( B ) TYPE: amino acid ( C ) STRANDEDNESS: unknown
( D ) TOPOLOGY: unknown ( i i ) MOLECULE TYPE: peptide ( v i i ) IMMEDIATE SOURCE:
  ( B ) CLONE: TEDFK-2A ( i x ) FEATURE: Amino acid 4 is aminoisobutyric acid (Aib)

( x i ) SEQUENCE DESCRIPTION: SEQ ID NO:45:

Arg Cys Val Xaa Val Arg Lys Gly Asn Cys Tyr Phe Lys
1               5                   10

( 2 ) INFORMATION FOR SEQ ID NO:46:

( i ) SEQUENCE CHARACTERISTICS:
    ( A ) LENGTH: 13 amino acids
    ( B ) TYPE: amino acid
    ( C ) STRANDEDNESS: unknown
    ( D ) TOPOLOGY: unknown ( i i ) MOLECULE TYPE: peptide ( v i i ) IMMEDIATE SOURCE:
    ( B ) CLONE: TEDFK-3A ( i x ) FEATURE: Amino acid 2 is aminoisobutyric acid (Aib)

( x i ) SEQUENCE DESCRIPTION: SEQ ID NO:46:

Arg Xaa Val Cys Val Arg Lys Gly Asn Cys Tyr Phe Lys
1               5                   10

( 2 ) INFORMATION FOR SEQ ID NO:47:

( i ) SEQUENCE CHARACTERISTICS:
    ( A ) LENGTH: 13 amino acids
    ( B ) TYPE: amino acid
    ( C ) STRANDEDNESS: unknown
    ( D ) TOPOLOGY: unknown ( i i ) MOLECULE TYPE: peptide ( v i i ) IMMEDIATE SOURCE:
    ( B ) CLONE: TEDFK-1,2A ( i x ) FEATURE: Amino acids 4 and 10 are aminoisobutyric acid
    (Aib)

( x i ) SEQUENCE DESCRIPTION: SEQ ID NO:47:

Arg Cys Val Xaa Val Arg Lys Gly Asn Xaa Tyr Phe Lys
1               5                   10

( 2 ) INFORMATION FOR SEQ ID NO:48:

( i ) SEQUENCE CHARACTERISTICS:
    ( A ) LENGTH: 13 amino acids
    ( B ) TYPE: amino acid
    ( C ) STRANDEDNESS: unknown
    ( D ) TOPOLOGY: unknown ( i i ) MOLECULE TYPE: peptide ( v i i ) IMMEDIATE SOURCE:
    ( B ) CLONE: M1

( x i ) SEQUENCE DESCRIPTION: SEQ ID NO:48:

Arg Cys Val Cys Val Arg Lys Gly Asn Cys Tyr Lys Lys
1               5                   10

( 2 ) INFORMATION FOR SEQ ID NO:49:

( i ) SEQUENCE CHARACTERISTICS:
    ( A ) LENGTH: 13 amino acids
    ( B ) TYPE: amino acid
    ( C ) STRANDEDNESS: unknown
    ( D ) TOPOLOGY: unknown ( i i ) MOLECULE TYPE: peptide ( v i i ) IMMEDIATE SOURCE:
    ( B ) CLONE: M2

( x i ) SEQUENCE DESCRIPTION: SEQ ID NO:49:

Arg Cys Val Cys Val Arg Lys Gly Asn Cys Tyr Pro Lys
1               5                   10

( 2 ) INFORMATION FOR SEQ ID NO:50:

( i ) SEQUENCE CHARACTERISTICS:
    ( A ) LENGTH: 13 amino acids
    ( B ) TYPE: amino acid
    ( C ) STRANDEDNESS: unknown
    ( D ) TOPOLOGY: unknown ( i i ) MOLECULE TYPE: peptide ( v i i ) IMMEDIATE SOURCE:
    ( B ) CLONE: M3

( x i ) SEQUENCE DESCRIPTION: SEQ ID NO:50:

Arg Cys Val Cys Val Arg Lys Gly Asn Cys Tyr Lys Phe
1               5                   10

( 2 ) INFORMATION FOR SEQ ID NO:51:

( i ) SEQUENCE CHARACTERISTICS:
    ( A ) LENGTH: 12 amino acids
    ( B ) TYPE: amino acid
    ( C ) STRANDEDNESS: unknown
    ( D ) TOPOLOGY: unknown ( i i ) MOLECULE TYPE: peptide ( v i i ) IMMEDIATE SOURCE:
    ( B ) CLONE: M4

( x i ) SEQUENCE DESCRIPTION: SEQ ID NO:51:

Arg Cys Val Cys Val Arg Lys Lys Cys Tyr Lys Lys
1               5                   10

( 2 ) INFORMATION FOR SEQ ID NO:52:

( i ) SEQUENCE CHARACTERISTICS:
    ( A ) LENGTH: 11 amino acids
    ( B ) TYPE: amino acid
    ( C ) STRANDEDNESS: unknown
    ( D ) TOPOLOGY: unknown ( i i ) MOLECULE TYPE: peptide ( v i i ) IMMEDIATE SOURCE:
    ( B ) CLONE: M5

( x i ) SEQUENCE DESCRIPTION: SEQ ID NO:52:

Lys Cys Val Cys Lys Lys Asn Cys Tyr Lys Lys
1               5                   10

( 2 ) INFORMATION FOR SEQ ID NO:53:

( i ) SEQUENCE CHARACTERISTICS:
    ( A ) LENGTH: 11 amino acids
    ( B ) TYPE: amino acid
    ( C ) STRANDEDNESS: unknown ( D ) TOPOLOGY: unknown ( i i ) MOLECULE TYPE: peptide ( v i i ) IMMEDIATE SOURCE:
    ( B ) CLONE: M6

( x i ) SEQUENCE DESCRIPTION: SEQ ID NO:53:

Lys Cys Val Cys Lys Lys Asn Cys Tyr Lys Lys
1               5                   10

( 2 ) INFORMATION FOR SEQ ID NO:54:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: M8

( i x ) FEATURE: Amino acid 8 is aminoisobutyric acid (Aib)

( x i ) SEQUENCE DESCRIPTION: SEQ ID NO:54:

Lys Cys Val Cys Val Lys Lys Xaa Tyr Phe Lys
1               5                   10

( 2 ) INFORMATION FOR SEQ ID NO:55:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: M9

( x i ) SEQUENCE DESCRIPTION: SEQ ID NO:55:

Arg Cys Val Cys Val Arg Lys Gly Asn Ile Tyr Phe Lys
1               5                   10

( 2 ) INFORMATION FOR SEQ ID NO:56:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: M10

( x i ) SEQUENCE DESCRIPTION: SEQ ID NO:56:

Arg Cys Val Cys Val Arg Lys Gly Asn Ser Tyr Phe Lys
1               5                   10

( 2 ) INFORMATION FOR SEQ ID NO:57:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
  ( B ) CLONE: M11

( x i ) SEQUENCE DESCRIPTION: SEQ ID NO:57:

Arg Cys Val Ser Val Arg Lys Gly Asn Cys Tyr Phe Lys
 1           5                   1 0

( 2 ) INFORMATION FOR SEQ ID NO:58:

( i ) SEQUENCE CHARACTERISTICS:
    ( A ) LENGTH: 13 amino acids
    ( B ) TYPE: amino acid
    ( C ) STRANDEDNESS: unknown
    ( D ) TOPOLOGY: unknown ( i i ) MOLECULE TYPE: peptide ( v i i ) IMMEDIATE SOURCE:
    ( B ) CLONE: M12

( i x ) FEATURE: Amino acid 2 is norleucine (Nle)

( x i ) SEQUENCE DESCRIPTION: SEQ ID NO:58:

Arg Xaa Val Cys Val Arg Lys Gly Asn Cys Tyr Phe Lys
 1           5                   1 0

( 2 ) INFORMATION FOR SEQ ID NO:59:

( i ) SEQUENCE CHARACTERISTICS:
    ( A ) LENGTH: 13 amino acids
    ( B ) TYPE: amino acid
    ( C ) STRANDEDNESS: unknown
    ( D ) TOPOLOGY: unknown ( i i ) MOLECULE TYPE: peptide ( v i i ) IMMEDIATE SOURCE:
    ( B ) CLONE: M13

( x i ) SEQUENCE DESCRIPTION: SEQ ID NO:59:

Arg Cys Ile Cys Ile Arg Lys Gly Asn Cys Tyr Phe Lys
 1           5                   1 0

( 2 ) INFORMATION FOR SEQ ID NO:60:

( i ) SEQUENCE CHARACTERISTICS:
    ( A ) LENGTH: 13 amino acids
    ( B ) TYPE: amino acid
    ( C ) STRANDEDNESS: unknown
    ( D ) TOPOLOGY: unknown ( i i ) MOLECULE TYPE: peptide ( v i i ) IMMEDIATE SOURCE:
    ( B ) CLONE: M14

( i x ) FEATURE: Amino acid 10 is aminoisobutyric acid (Aib)

( x i ) SEQUENCE DESCRIPTION: SEQ ID NO:60:

Arg Cys Val Ile Val Arg Lys Gly Asn Xaa Tyr Phe Lys
 1           5                   1 0

( 2 ) INFORMATION FOR SEQ ID NO:61:

( i ) SEQUENCE CHARACTERISTICS:
    ( A ) LENGTH: 13 amino acids
    ( B ) TYPE: amino acid
    ( C ) STRANDEDNESS: unknown
    ( D ) TOPOLOGY: unknown -continued (  i  i  ) MOLECULE TYPE: peptide (  v  i  i  ) IMMEDIATE SOURCE:
  (  B  ) CLONE: M15

(  x  i  ) SEQUENCE DESCRIPTION: SEQ ID NO:61:

Lys Lys Arg Cys Val Cys Val Arg Lys Gly Asn Cys Tyr
1               5                           10

(  2  ) INFORMATION FOR SEQ ID NO:62:

(  i  ) SEQUENCE CHARACTERISTICS:
    (  A  ) LENGTH: 13 amino acids
    (  B  ) TYPE: amino acid
    (  C  ) STRANDEDNESS: unknown
    (  D  ) TOPOLOGY: unknown (  i  i  ) MOLECULE TYPE: peptide (  v  i  i  ) IMMEDIATE SOURCE:
    (  B  ) CLONE: M16

(  x  i  ) SEQUENCE DESCRIPTION: SEQ ID NO:62:

Lys Arg Cys Val Cys Val Arg Lys Gly Asn Cys Tyr Lys
1               5                           10

(  2  ) INFORMATION FOR SEQ ID NO:63:

(  i  ) SEQUENCE CHARACTERISTICS:
    (  A  ) LENGTH: 13 amino acids
    (  B  ) TYPE: amino acid
    (  C  ) STRANDEDNESS: unknown
    (  D  ) TOPOLOGY: unknown (  i  i  ) MOLECULE TYPE: peptide (  v  i  i  ) IMMEDIATE SOURCE:
    (  B  ) CLONE: M17

(  i  x  ) FEATURE: Amino acid 10 is aminoisobutyric acid (Aib)

(  x  i  ) SEQUENCE DESCRIPTION: SEQ ID NO:63:

Arg Cys Val Cys Val Arg Lys Gly Lys Xaa Tyr Phe Lys
1               5                           10

(  2  ) INFORMATION FOR SEQ ID NO:64:

(  i  ) SEQUENCE CHARACTERISTICS:
    (  A  ) LENGTH: 13 amino acids
    (  B  ) TYPE: amino acid
    (  C  ) STRANDEDNESS: unknown
    (  D  ) TOPOLOGY: unknown (  i  i  ) MOLECULE TYPE: peptide (  v  i  i  ) IMMEDIATE SOURCE:
    (  B  ) CLONE: M18

(  x  i  ) SEQUENCE DESCRIPTION: SEQ ID NO:64:

Arg Cys Val Cys Val Arg Lys Gly Asp Cys Tyr Phe Lys
1               5                           10

(  2  ) INFORMATION FOR SEQ ID NO:65:

(  i  ) SEQUENCE CHARACTERISTICS:
    (  A  ) LENGTH: 13 amino acids
    (  B  ) TYPE: amino acid
    (  C  ) STRANDEDNESS: unknown
    (  D  ) TOPOLOGY: unknown (  i  i  ) MOLECULE TYPE: peptide ( v i i ) IMMEDIATE SOURCE:
    ( B ) CLONE: M19

( i x ) FEATURE: Amino acid 10 is aminoisobutyric acid (Aib)

( x i ) SEQUENCE DESCRIPTION: SEQ ID NO:65:

Lys Phe Val Phe Val Lys Lys Gly Asn Xaa Tyr Phe Lys
1               5                   10

( 2 ) INFORMATION FOR SEQ ID NO:66:

( i ) SEQUENCE CHARACTERISTICS:
      ( A ) LENGTH: 12 amino acids
      ( B ) TYPE: amino acid
      ( C ) STRANDEDNESS: unknown
      ( D ) TOPOLOGY: unknown ( i i ) MOLECULE TYPE: peptide ( v i i ) IMMEDIATE SOURCE:
      ( B ) CLONE: M21

( x i ) SEQUENCE DESCRIPTION: SEQ ID NO:66:

Lys Cys Ile Cys Ile Lys Lys Asn Ile Ile Ile Lys
1               5                   10

( 2 ) INFORMATION FOR SEQ ID NO:67:

( i ) SEQUENCE CHARACTERISTICS:
      ( A ) LENGTH: 13 amino acids
      ( B ) TYPE: amino acid
      ( C ) STRANDEDNESS: unknown
      ( D ) TOPOLOGY: unknown ( i i ) MOLECULE TYPE: peptide ( v i i ) IMMEDIATE SOURCE:
      ( B ) CLONE: M25

( i x ) FEATURE: Amino acid 4 is aminoisobutyric acid (Aib)

( x i ) SEQUENCE DESCRIPTION: SEQ ID NO:67:

Lys Cys Val Xaa Val Arg Lys Gly Asn Cys Tyr Phe Lys
1               5                   10

( 2 ) INFORMATION FOR SEQ ID NO:68:

( i ) SEQUENCE CHARACTERISTICS:
      ( A ) LENGTH: 13 amino acids
      ( B ) TYPE: amino acid
      ( C ) STRANDEDNESS: unknown
      ( D ) TOPOLOGY: unknown ( i i ) MOLECULE TYPE: peptide ( v i i ) IMMEDIATE SOURCE:
      ( B ) CLONE: M26

( x i ) SEQUENCE DESCRIPTION: SEQ ID NO:68:

Arg Cys Val Cys Val Arg Lys Gly Asn Cys Tyr Trp Lys
1               5                   10

( 2 ) INFORMATION FOR SEQ ID NO:69:

( i ) SEQUENCE CHARACTERISTICS:
      ( A ) LENGTH: 13 amino acids
      ( B ) TYPE: amino acid
      ( C ) STRANDEDNESS: unknown
      ( D ) TOPOLOGY: unknown ( i i ) MOLECULE TYPE: peptide (v i i) IMMEDIATE SOURCE:
     (B) CLONE: M27

(x i) SEQUENCE DESCRIPTION: SEQ ID NO:69:

Arg Cys Val Trp Val Arg Lys Gly Asn Cys Tyr Phe Lys
 1               5                   10

(2) INFORMATION FOR SEQ ID NO:70:

(i) SEQUENCE CHARACTERISTICS:
     (A) LENGTH: 13 amino acids
     (B) TYPE: amino acid
     (C) STRANDEDNESS: unknown
     (D) TOPOLOGY: unknown (i i) MOLECULE TYPE: peptide (v i i) IMMEDIATE SOURCE:
     (B) CLONE: M28

(x i) SEQUENCE DESCRIPTION: SEQ ID NO:70:

Arg Trp Val Cys Val Arg Lys Gly Asn Cys Tyr Phe Lys
 1               5                   10

(2) INFORMATION FOR SEQ ID NO:71:

(i) SEQUENCE CHARACTERISTICS:
     (A) LENGTH: 13 amino acids
     (B) TYPE: amino acid
     (C) STRANDEDNESS: unknown
     (D) TOPOLOGY: unknown (i i) MOLECULE TYPE: peptide (v i i) IMMEDIATE SOURCE:
     (B) CLONE: M29

(x i) SEQUENCE DESCRIPTION: SEQ ID NO:71:

Arg Cys Val Cys Val Arg Lys Gly Asn Cys Tyr Phe Trp
 1               5                   10

(2) INFORMATION FOR SEQ ID NO:72:

(i) SEQUENCE CHARACTERISTICS:
     (A) LENGTH: 13 amino acids
     (B) TYPE: amino acid
     (C) STRANDEDNESS: unknown
     (D) TOPOLOGY: unknown (i i) MOLECULE TYPE: peptide (v i i) IMMEDIATE SOURCE:
     (B) CLONE: M30

(x i) SEQUENCE DESCRIPTION: SEQ ID NO:72:

Arg Cys Val Cys Val Arg Lys Trp Asn Cys Tyr Phe Lys
 1               5                   10

(2) INFORMATION FOR SEQ ID NO:73:

(i) SEQUENCE CHARACTERISTICS:
     (A) LENGTH: 13 amino acids
     (B) TYPE: amino acid
     (C) STRANDEDNESS: unknown
     (D) TOPOLOGY: unknown (i i) MOLECULE TYPE: peptide (v i i) IMMEDIATE SOURCE:
     (B) CLONE: M31

(x i) SEQUENCE DESCRIPTION: SEQ ID NO:73:

Trp Cys Val Cys Val Arg Lys Gly Asn Cys Tyr Phe Lys
1               5                   10

(2) INFORMATION FOR SEQ ID NO:74:

(i) SEQUENCE CHARACTERISTICS:
        (A) LENGTH: 11 amino acids
        (B) TYPE: amino acid
        (C) STRANDEDNESS: unknown
        (D) TOPOLOGY: linear (ii) MOLECULE TYPE: peptide (vii) IMMEDIATE SOURCE:
        (B) CLONE: M20

(ix) FEATURE: Amino acid 8 is aminoisobutyric acid (Aib)

(xi) SEQUENCE DESCRIPTION: SEQ ID NO:74:

Lys Phe Val Phe Val Lys Lys Xaa Tyr Phe Lys
1               5                   10

(2) INFORMATION FOR SEQ ID NO:75:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: peptide (vii) IMMEDIATE SOURCE:
        (B) CLONE: M22

(xi) SEQUENCE DESCRIPTION: SEQ ID NO:75:

Lys Phe Val Phe Val Lys Lys Ile Tyr Lys Lys
1               5                   10

(2) INFORMATION FOR SEQ ID NO:76:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (vii) IMMEDIATE SOURCE:
        (B) CLONE: M23

(xi) SEQUENCE DESCRIPTION: SEQ ID NO:76:

Lys Phe Val Phe Val Lys Lys Ile Tyr Lys
1               5                   10

(2) INFORMATION FOR SEQ ID NO:77:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (vii) IMMEDIATE SOURCE:
        (B) CLONE: M24

(xi) SEQUENCE DESCRIPTION: SEQ ID NO:77:

Lys Phe Val Phe Val Lys Lys Ile Tyr Lys Lys Lys ( 2 ) INFORMATION FOR SEQ ID NO:78:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: M35

( x i ) SEQUENCE DESCRIPTION: SEQ ID NO:78:

```
Lys  Lys  Ile  Tyr  Lys  Lys  Ile  Tyr  Lys  Lys
1                 5                        10
```

( 2 ) INFORMATION FOR SEQ ID NO:79:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: M36

( x i ) SEQUENCE DESCRIPTION: SEQ ID NO:79:

```
Lys  Val  Phe  Val  Phe  Lys  Phe  Val  Phe  Val  Lys
1                 5                        10
```

( 2 ) INFORMATION FOR SEQ ID NO:80:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: M32

( x i ) SEQUENCE DESCRIPTION: SEQ ID NO:80:

```
Lys  Phe  Val  Phe  Val  Ile  Tyr  Lys  Lys  Lys  Lys
1                 5                        10
```

( 2 ) INFORMATION FOR SEQ ID NO:81:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: unknown ( i i ) MOLECULE TYPE: peptide ( v i i ) IMMEDIATE SOURCE:
        ( B ) CLONE: M33

( x i ) SEQUENCE DESCRIPTION: SEQ ID NO:81:

```
Lys  Phe  Val  Phe  Val  Ile  Tyr  Lys  Lys  Lys
1                 5                        10
```

( 2 ) INFORMATION FOR SEQ ID NO:82:

( i ) SEQUENCE CHARACTERISTICS:
   ( A ) LENGTH: 9 amino acids
   ( B ) TYPE: amino acid
   ( C ) STRANDEDNESS: unknown
   ( D ) TOPOLOGY: unknown ( i i ) MOLECULE TYPE: peptide ( v i i ) IMMEDIATE SOURCE:
   ( B ) CLONE: M34

( x i ) SEQUENCE DESCRIPTION: SEQ ID NO:82:

Lys Phe Val Phe Val Ile Tyr Lys Lys
1               5

( 2 ) INFORMATION FOR SEQ ID NO:83:

( i ) SEQUENCE CHARACTERISTICS:
      ( A ) LENGTH: 8 amino acids
      ( B ) TYPE: amino acid
      ( C ) STRANDEDNESS: unknown
      ( D ) TOPOLOGY: unknown ( i i ) MOLECULE TYPE: peptide ( v i i ) IMMEDIATE SOURCE:
      ( B ) CLONE: M37

( x i ) SEQUENCE DESCRIPTION: SEQ ID NO:83:

Lys Phe Val Phe Val Ile Tyr Lys
1               5

( 2 ) INFORMATION FOR SEQ ID NO:84:

( i ) SEQUENCE CHARACTERISTICS:
      ( A ) LENGTH: 13 amino acids
      ( B ) TYPE: amino acid
      ( C ) STRANDEDNESS: unknown
      ( D ) TOPOLOGY: unknown ( i i ) MOLECULE TYPE: peptide ( v i i ) IMMEDIATE SOURCE:
      ( B ) CLONE: Enantiomer of TEDFK ( i x ) FEATURE: All amino acids are D-amino acids ( x i ) SEQUENCE DESCRIPTION: SEQ ID NO:84:

Arg Cys Val Cys Val Arg Lys Gly Asn Cys Tyr Phe Lys
1               5                   10

( 2 ) INFORMATION FOR SEQ ID NO:85:

( i ) SEQUENCE CHARACTERISTICS:
      ( A ) LENGTH: 13 amino acids
      ( B ) TYPE: amino acid
      ( C ) STRANDEDNESS: unknown
      ( D ) TOPOLOGY: unknown ( i i ) MOLECULE TYPE: peptide ( v i i ) IMMEDIATE SOURCE:
      ( B ) CLONE: Retro-inverso of TEDFK ( i x ) FEATURE: All amino acids are D-amino acids ( x i ) SEQUENCE DESCRIPTION: SEQ ID NO:85:

Lys Phe Tyr Cys Asn Gly Lys Arg Val Cys Val Cys Arg
1               5                   10

( 2 ) INFORMATION FOR SEQ ID NO:86:

(i) SEQUENCE CHARACTERISTICS:
   (A) LENGTH: 11 amino acids
   (B) TYPE: amino acid
   (C) STRANDEDNESS: unknown
   (D) TOPOLOGY: unknown (ii) MOLECULE TYPE: peptide (vii) IMMEDIATE SOURCE:
   (B) CLONE: KLK (xi) SEQUENCE DESCRIPTION: SEQ ID NO:86:

```
Lys  Leu  Lys  Leu  Leu  Leu  Leu  Leu  Lys  Leu  Lys
 1              5                        10
```